(12) United States Patent
Borgersen et al.

(10) Patent No.: US 6,400,992 B1
(45) Date of Patent: Jun. 4, 2002

(54) CO-EXTRUDED, MULTI-LUMEN MEDICAL LEAD

(75) Inventors: Svenn E. Borgersen, Eagan, MN (US); Hans W. Kramer, Temucula, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/271,498

(22) Filed: Mar. 18, 1999

(51) Int. Cl.$^7$ .................................................. A61N 1/05
(52) U.S. Cl. ...................................................... 607/122
(58) Field of Search ................................ 607/116, 119, 607/122, 123, 125

(56) References Cited

U.S. PATENT DOCUMENTS

| | | | |
|---|---|---|---|
| 4,484,586 A | 11/1984 | Mcmickle et al. |
| 4,608,986 A | 9/1986 | Beranek et al. |
| 4,640,983 A | 2/1987 | Comte |
| 4,790,831 A | 12/1988 | Skribiski |
| 4,873,308 A | 10/1989 | Coury et al. |
| 4,964,414 A | 10/1990 | Handa et al. |
| 5,007,435 A | 4/1991 | Doan et al. |
| 5,109,077 A | 4/1992 | Wick |
| 5,133,742 A | 7/1992 | Pinchuk |
| 5,246,014 A | 9/1993 | Williams et al. |
| 5,318,041 A | 6/1994 | DuBois et al. |
| 5,324,321 A | 6/1994 | Pohndorf et al. |
| 5,374,245 A | 12/1994 | Mahurkar |
| 5,419,921 A | 5/1995 | Molacek et al. |
| 5,451,206 A | 9/1995 | Young |
| 5,456,674 A | 10/1995 | Bos et al. |
| 5,483,022 A | 1/1996 | Mar |
| 5,545,203 A | 8/1996 | Doan |
| 5,584,873 A | 12/1996 | Shoberg et al. |
| 5,622,665 A | 4/1997 | Wang |
| 5,624,617 A | 4/1997 | Sorabella et al. |
| 5,676,694 A | 10/1997 | Boser et al. |
| 5,702,372 A | 12/1997 | Nelson |
| 5,760,341 A | 6/1998 | Laske et al. |

FOREIGN PATENT DOCUMENTS

| | | | |
|---|---|---|---|
| EP | 0009732 | 9/1979 | ............ A61N/1/04 |
| EP | 0783900 | 7/1997 | ............ A61N/1/05 |

Primary Examiner—William E. Kamm
(74) Attorney, Agent, or Firm—Girma Wolde-Michael

(57) ABSTRACT

Medical electrical leads for sensing or electrical stimulation of body organs or tissues, particularly implantable cardiac leads for delivering pacing pulses and cardioversion/defibrillation shocks, and/or sensing the cardiac electrogram (EGM) or other physiologic data and their methods of fabrication are disclosed. A lead body sheath is co-extruded in a co-extrusion process using bio-compatible, electrically insulating, materials of differing durometers in differing axial sections thereof, resulting in a unitary lead body sheath having differing stiffness sections including axial segments or webs or lumen encircling rings or other structures in its cross-section. The lead body sheath is co-extruded to have an outer surface adapted to be exposed to the environment or to be enclosed within an outer sheath and to have a plurality of lead conductor lumens for receiving and enclosing a like plurality of lead conductors of the same or differing types. The lead body sheath can be co-extruded of a plurality of sheath segments containing a lead conductor lumen and formed of a first durometer material or of differing durometer materials. A web of a further durometer material can be co-extruded extending between the adjoining boundaries of the axial sheath segments and bonding the adjacent segments together. The lead body sheath can be tailored to exhibit differing bending stiffnesses away from the lead body sheath axis in selected polar directions around 360° circumference of the sheath body.

21 Claims, 6 Drawing Sheets

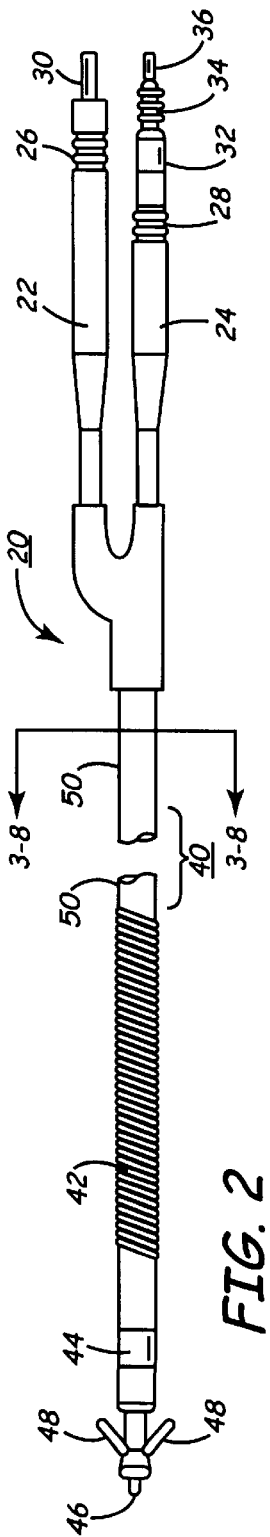
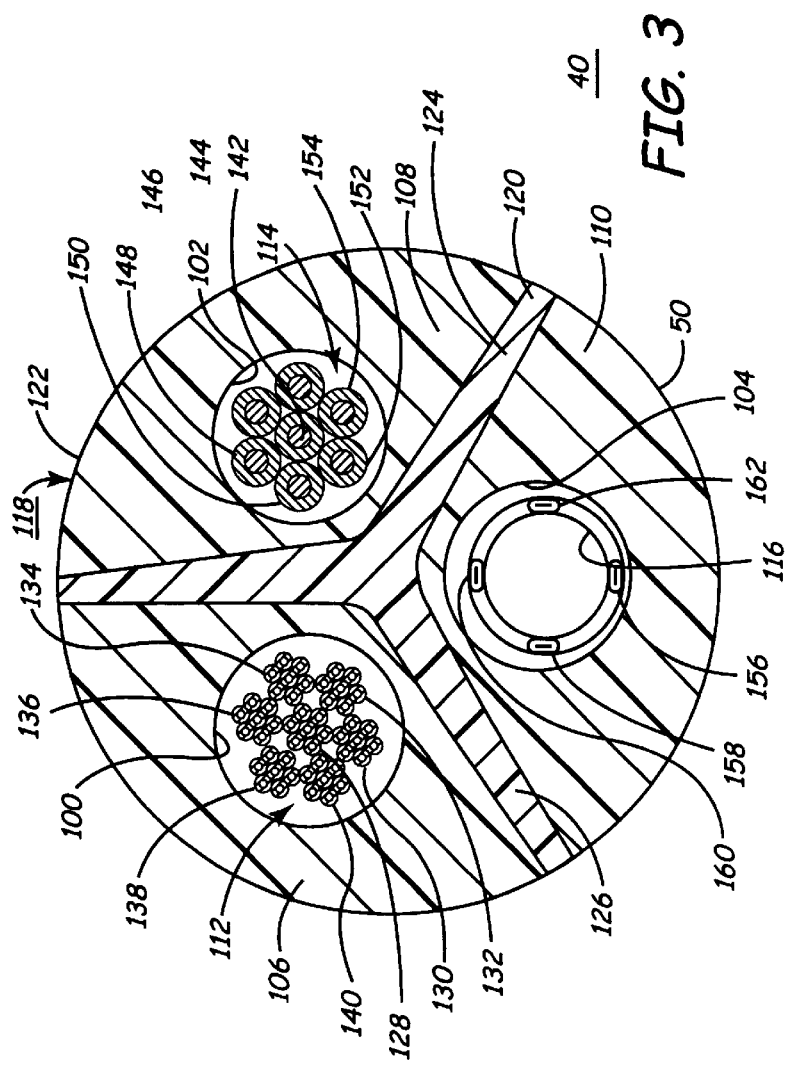

CO-EXTRUDED, MULTI-LUMEN MEDICAL LEAD

CROSS-REFERENCE TO RELATED APPLICATION

Reference is hereby made to commonly assigned, U.S. patent application Ser. No. 08/990,647 filed Dec. 15, 1997, now U.S. Pat. No. 5,935,139 for MEDICAL ELECTRICAL LEAD in the name of Alan Rausch et al.

FIELD OF THE INVENTION

The present invention relates to medical electrical leads for sensing or electrical stimulation of body organs or tissues and their method of fabrication, such leads having multiple electrical conductors encased in a lead body, and particularly to implantable cardiac leads for delivering electrical stimulation to the heart, e.g., pacing pulses and cardioversion/defibrillation shocks, and/or sensing the cardiac electrogram (EGM) or other physiologic data.

BACKGROUND OF THE INVENTION

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters of the body. A pacemaker or cardioverter/defibrillator implantable pulse generator (IPG) or a cardiac monitor is typically coupled to the heart through one or more of such endocardial leads. The proximal end of such leads typically is formed with a connector which connects to a terminal of the IPG or monitor. The lead body typically comprises one or more insulated, conductive wire surrounded by an insulating outer sleeve. Each conductive wire couples a proximal lead connector element with a distal stimulation and/or sensing electrode. An endocardial cardiac lead having a single stimulation and/or sensing electrode at the distal lead end and a single conductive wire is referred to as a unipolar lead. An endocardial cardiac lead having two or more stimulation and/or sensing electrodes at the distal lead end and two or more conductive wires is referred to as a bipolar lead or a multi-polar lead, respectively.

In order to implant an endocardial lead within a heart chamber, a transvenous approach is utilized wherein the lead is inserted into and passed through a pathway comprising the subclavian, jugular, or cephalic vein and through the superior vena cava into the right atrium or ventricle. It is necessary to accurately position the sense and/or stimulation electrode surface against the endocardium or within the myocardium at the desired site in order to achieve reliable sensing of the cardiac electrogram and/or to apply stimulation that effectively paces or cardioverts the heart chamber. The desired heart sites include the right atrium, typically the right atrial appendage, the right ventricle, typically the ventricular apex, and the coronary sinus and great vein.

The transvenous pathway can include a number of twists and turns, and the lead body can be forced against bony structures of the body that apply stress to it. Moreover, the heart beats approximately 100,000 times per day or over 30 million times a year, and each beat stresses at least the distal portion of the lead body. The lead conductors and insulation are subjected to cumulative mechanical stresses, as well as material reactions as described below, that can result in degradation of the insulation or fractures of the lead conductors with untoward effects on device performance and patient well being.

Early implantable, endocardial and epicardial, bipolar cardiac pacing leads employed separate coiled wire conductors in a side by side configuration within a silicone rubber sheath and incorporated a lumen for receiving a stiffening stylet inside the lumen of at least one of the conductor coils to facilitate advancement through the transvenous pathway. The stiffening stylet was advanced through a proximal connector pin opening to stiffen the lead body during the transvenous introduction and location of the distal electrodes deeply inserted into the right ventricular apex and was then withdrawn. The relatively large diameter and stiff lead body provided column strength that was relied upon to maintain the distal electrodes embedded into the trabeculae of the right ventricular apex. Fibrous tissue growth about the distal lead body was also relied upon to hold the distal pace/sense electrodes in position.

Similar atrial, J-shaped lead bodies were developed that relied upon the lead body stiffness and shape to lodge and maintain distal pace/sense electrodes lodged into the right atrial appendage after the stiffening stylet was removed from the lead conductor lumen. In the case of early J-shaped atrial leads formed of silicone rubber, the lead body was reinforced with an outward extending silicone rubber rib to maintain the J-shape bend when the stylet was removed. In later J-shaped atrial leads, internally encased metal coils or wires have been employed to maintain the J-shape bend.

Such relatively large and stiff lead bodies were disadvantageous in a number of respects. The available biocompatible conductor material alloy presented an impedance that limited current carrying capacity. The large diameter body made it difficult to implant more than one lead through the venous system. The relatively high column strength was often still insufficient to maintain the pace/sense electrodes in the atrial appendage or ventricular apex, and physicians often resorted to leaving the stylets in place, resulting in fracture of the lead conductor and lead body sheath when the stylet wire broke. Once the lead bodies fibrosed in, they were difficult to retract from the heart if they needed to be replaced. Finally, the lead conductors tended to fracture at stress sites, in bipolar leads sometimes due to stresses applied unevenly to the side-by-side arrangement of the conductor coils.

In the efforts to solve these problems, more flexible lead bodies were developed using smaller diameter coiled wire conductors and other insulating materials, most notably polyurethane compositions. Passive and active fixation mechanisms incorporated were into the distal end of the endocardial lead to fix the electrode at a desired site in a heart chamber during the acute post-operative phase before fibrous tissue growth envelops the lead body. Passive fixation mechanisms, e.g., a plurality of soft, pliant tines that bear against the trabeculae in the right ventricle or the atrial appendage to urge the distal tip electrode against the endocardium, do not invade the myocardium. Active fixation mechanisms are designed to penetrate the endocardial surface and lodge in the myocardium without perforating through the epicardium or into an adjoining chamber. The most widely used active fixation mechanism employs a sharpened helix, which typically also constitutes the distal tip electrode, that is adapted to be rotated by some means from the proximal end of the lead outside the body in order to screw the helix into the myocardium and permanently fix the electrode at the desired atrial or ventricular site.

The side by side, bipolar, coiled wire lead body design was also replaced by a coaxial configuration which is more resistant to fracture and smaller in diameter and which was typically formed of polyurethane or silicone rubber inner and outer sheathes. More recently, each such coiled wire conductor of both unipolar and bipolar leads was formed of a plurality of multi-filar, parallel-wound, coiled wire conductors electrically connected in common in an electrically redundant fashion as shown in commonly assigned U.S. Pat. No. 5,007,435, for example, incorporated herein by reference. Such redundant coiled wire conductors of bipolar and multi-polar lead bodies are coaxially arranged about the stiffening stylet receiving lumen and insulated from one another by coaxially arranged insulating sheaths separating each coiled wire conductor from the adjacent coiled wire conductor(s).

In the implantation of a cardiac device of the types listed above, and in the replacement of previously implanted cardiac leads, two or more transvenous cardiac leads are typically introduced through the venous system into the right chambers or coronary sinus of the heart. It has long been desired to minimize the diameter of the transvenous cardiac lead body to facilitate the introduction of several cardiac leads by the same transvenous approach. Moreover, a number of multi-polar, endocardial cardiac leads have been designed to accommodate more than two electrodes or to make electrical connection with other components, e.g., blood pressure sensors, temperature sensors, pH sensors, or the like, in the distal portion of the lead. In addition, endocardial cardioversion/defibrillation leads were developed for unipolar or bipolar pacing and sensing functions and for delivering cardioversion/defibrillation shocks to a heart chamber intended to be implanted in a heart chamber or a cardiac blood vessel, e.g., the coronary sinus. The increased number of separate polarity and insulated coiled wire conductors is difficult to accommodate in the conventional coaxial coiled wire conductor winding arrangement having a desired, small, lead body outer diameter. One approach involved the use of separately insulated, coiled wire conductors that are parallel-wound with a common diameter and are separately coupled between a proximal connector element and to a distal electrode or terminal as disclosed in commonly assigned U.S. Pat. No. 5,796,044, incorporated herein by reference.

Moreover, the use of thin polyurethane inner and outer sheathes along with certain lead conductor alloys became problematic as the bio-stability of such lead materials in chronic implantation came into question as described in commonly assigned U.S. Pat. No. 5,419,921. In general, it is acknowledged that there are a number of mechanisms for degradation of elastomeric polyurethane pacing leads in vivo. One is environmental stress cracking (ESC), the generation of crazes or cracks in the polyurethane elastomer produced by the combined interaction of a medium capable of acting on the elastomer and a stress level above a specific threshold. Another is metal ion induced oxidation (MIO) in which polyether urethane elastomers exhibit accelerated degradation from metal ions such as cobalt ions, chromium ions, molybdenum ions and the like which are used alone or in alloys in pacing lead conductors. As explained therein, certain polyurethane elastomers that have desirable characteristics for lead bodies are more susceptible to ESC and MIO degradation than others that are less desirable. In the '921 patent, the polyurethane elastomers that are susceptible to ESC and MIO degradation are coated or co-extruded with the less susceptible polyurethane elastomers to form tubular sheaths having their inner and outer surfaces protected by a less susceptible material layer.

All of the above considerations as to the increased complexity of the leads, the number of leads implanted in a common path, and desire to advance leads deep in the relatively small diameter coronary veins have led to efforts to at least not increase and optimally to decrease the overall diameter of the cardiac lead body without sacrificing bio-stability, resistance to crushing forces, and usability. It has been proposed to diminish the lead body further by eliminating the lumen for receiving the stiffening stylet and by replacing the large diameter coiled wire conductors with highly conductive miniaturized coiled wire conductors, stranded filament wires, or cables formed of a plurality of such stranded filament wires. In bipolar or multi-polar leads, each such wire or cable extends through a separate lumen extending in parallel within a lead body sheath that maintains electrical isolation between them.

Examples of such lead body insulating sheaths formed to enclose a plurality of straight, typically stranded, wire lead conductors, miniaturized coiled wire conductors or combinations of such straight and coiled wire conductors are disclosed in U.S. Pat. Nos. 4,608,986, 5,324,321, 5,545,203, and 5,584,873, all incorporated herein by reference. These patents and U.S. Pat. Nos. 4,640,983, 4,964,414, 5,246,014, 5,483,022, and 5,760,341, all incorporated herein by reference, present a number of alternative designs of such stranded filament wires or cables.

In the '873 patent, a unitary lead body insulating sheath is extruded having a plurality of spaced apart, outer lead conductor lumens that extend longitudinally and in parallel to one another for receiving coiled and/or straight wire conductors extending therethrough. The sheath is extruded in a single piece of a single material, and a like plurality of compression lumens that are preferably tear drop shaped are formed and extend longitudinally between the conductor lumens that absorb compression force that otherwise would crush a solid extruded lead body sheath. In certain embodiments an inner, centrally disposed lumen is formed in the lead body sheath that can be employed as a lead conductor lumen or as a compression lumen that can be made large enough in diameter to receive a stiffening stylet during introduction of the lead.

The above-referenced U.S. patent application Ser. No. 08/990,647 discloses a lead body sheath formed of separate parts including an extruded strut member or core and a separately extruded tubular outer tube. The core is extruded to form a plurality of longitudinally extending grooves in which lead conductors may be located and the assembly of the core and lead conductors is fitted within the lumen of the outer tube which thereby encloses the core and holds the conductors in the grooves. This construction simplifies the manufacture of the lead bodies, as it allows the conductors simply to be laid in the elongated grooves of the core rather than requiring that they be pushed or pulled along the lengths of pre-formed lumens. In some embodiments, the core is provided with a central, reinforcing strand, extending along the length of the lead body, providing for structural integrity and high tensile strength. The core may be manufactured as a single extrusion, extending the entire length of the lead body, or may take the form of sequentially aligned multiple extrusions of differing materials to provide for differential stiffness along the length of the lead.

In all of these lead body designs, the adjacent conductor lumens are separated from one another by very thin webs of the extruded insulating material. Despite these improvements, the cumulative affects of applied bending stresses can cause the extruded insulation webs of the lead body to split, thereby allowing the adjacent lead conductors to contact one another and to short-circuit the electrodes they are connected with. Each conductor lumen except for a centrally disposed conductor lumen is also separated from the outer surface of the insulating body sheath by a thin web. This outer thin web can also split, exposing the conductor to body fluids and tissues. The loss of support of the lead conductors upon splitting of the lead body sheath webs can also result in excessive bending and eventual fracture of the conductor. This problem is exacerbated when lead conductors of differing types each having a differing bending stiffness are enclosed in the outer lead conductor lumens leading to a lead body that is more flexible when bent in one direction than when bent in another direction.

SUMMARY OF THE INVENTION

The present invention addresses these problems by forming a lead body comprising an electrically insulating lead body sheath enclosing one or more lead conductors and separating the lead conductors from contacting one another. The lead body sheath is co-extruded in a co-extrusion process using bio-compatible, electrically insulating, materials of differing durometers in differing axial sections thereof, resulting in a unitary lead body sheath having differing stiffness axial sections including axial segments or webs or lumen encircling rings or other structures in its cross-section. The selection of the durometer of the materials and the configuration of the co-extruded lead body sheath sections may be used to control the geometric properties—e.g. bending stiffness, torsional stiffness, axial tension-compression stiffness, shear stiffness, and transverse compression stiffness of the lead body sheath. The lead body sheath is co-extruded to have an outer surface adapted to be exposed to the environment or to be enclosed within a further outer sheath and to have a plurality of lead conductor containing lumens for receiving and enclosing a like plurality or a fewer number of lead conductors.

In one embodiment, the lead body is co-extruded of a plurality of sheath segments, each segment containing a lead conductor lumen and formed of a first durometer material, and of a web of a second durometer material extending between the adjoining boundaries of the sheath segments. The web bonds with the adjacent segment boundaries to form the unitary lead body insulating sheath. The web may be formed by co-extrusion of a higher durometer material than the first durometer material.

In a further embodiment, the lead body sheath is co-extruded of a plurality of sheath segments, wherein each sheath segment contains a lead conductor lumen and is formed of a selected durometer material, whereby the lead body sheath can be tailored to exhibit differing bending stiffness away from the lead body sheath axis in selected polar directions around the 360° circumference of the sheath body.

This embodiment is particularly suitable for use with lead conductors of differing types that have differing bending stiffnesses. In one application of this embodiment, the durometer of the sheath segments are selected in relation to the lead conductor to compensate for the lead conductor bending stiffness. For example, relatively stiff lead conductors can be enclosed in segment lumens formed within segments of relatively low stiffness due to relatively low durometer materials, whereas relatively flexible lead conductors can be enclosed in segment lumens formed within segments of relatively high stiffness due to relatively high durometer materials. In this way, the bending stiffness of the lead body in all polar directions through 360° can be brought into equilibrium.

In a further application of this embodiment, it may be desired to form a lead body that does exhibit a bias to bend more readily in one polar direction than in the other directions. In this case, one of the sheath segments can be co-extruded of a more flexible material than the other sheath segments, and can enclose a relatively flexible lead conductor within that sheath segment lumen.

In a third embodiment, the web of the first embodiment and the differing stiffness sheath segment materials of the second embodiment can be advantageously combined. In this way, additional control of cross section geometric properties may be achieved by the use of different durometer materials not only for the sheath/webs, but also for each sheath segment around the cross section of extruded lead body material containing the lumens.

The sheath segments are preferably shaped as arcuate sections of the generally circular cross-section insulating sheath, and each preferably encloses a single lead conductor lumen. In a fourth embodiment, a centrally located lead conductor and/or stiffening stylet receiving lumen can also be formed of the same or differing durometer material as the sheath segments of the first or second embodiment or surrounded by the web material of the first or third embodiment.

In these embodiments of the invention, the adjoining boundaries of the longitudinally extending sheath segments with one another or with an intervening web are in intimate physical contact and bonded with one another in the co-extrusion process.

Thus, the co-extruded lead body sheath may be constructed in a variety of ways and may or may not be enclosed in a co-extruded outer sheath. The lead body sheath may contain a plurality of lumens either empty or containing electrical conductors, with or without a co-extruded sheaths surrounding each lumen. The lead body sheath may be co-extruded in sheath segments, sheath each segment connected by a radially oriented co-extruded sheath of various geometries which may or may not contact sheaths lining the lumens.

The co-extrusion of lead body sheath allows for selective control of lead body stiffness for bending, torsion, axial tension or compression, shear and transverse compression over the full length of the lead body or for a localized portion of the lead body length. Moreover, it allows the sheath segments and/or webs to act as barriers to prevent crack propagation in the lead body sheath which might lead to electrical contact between the lead conductors producing a short or incorrect signals, or cracking to the outer surface allowing the electrical lead conductors to be damaged by exposure to body fluids.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 2 is a plan view of a typical endocardial pacing and cardioversion/defibrillation lead that incorporates the lead conductors of the present invention; and FIGS. 3–8 are cross-section views of the lead body of the exemplary lead of FIG. 2 illustrating various embodiments and variations of embodiments of the present invention.

DETAILED DESCRIPTION OF THE PREFERRED EMBODIMENTS OF THE INVENTION

The present invention finds particular utility in the fabrication and implantation of cardiac leads, e.g., atrial and/or ventricular pacing leads and/or cardioversion/defibrillation leads having elongated lead bodies and lead conductors that are subject to fracture. Preferred embodiments of such lead conductor fabrications of such endocardial cardiac leads that are implanted transvenously will be described in detail. But, it is to be understood that the present invention is not limited to the same. The present invention can be implemented in the fabrication and use of other epicardial cardiac leads that are implanted subcutaneously and in electrical leads intended to be disposed within the patient's body, including nerve, brain, organ, and muscle stimulation leads.

Figure 1:
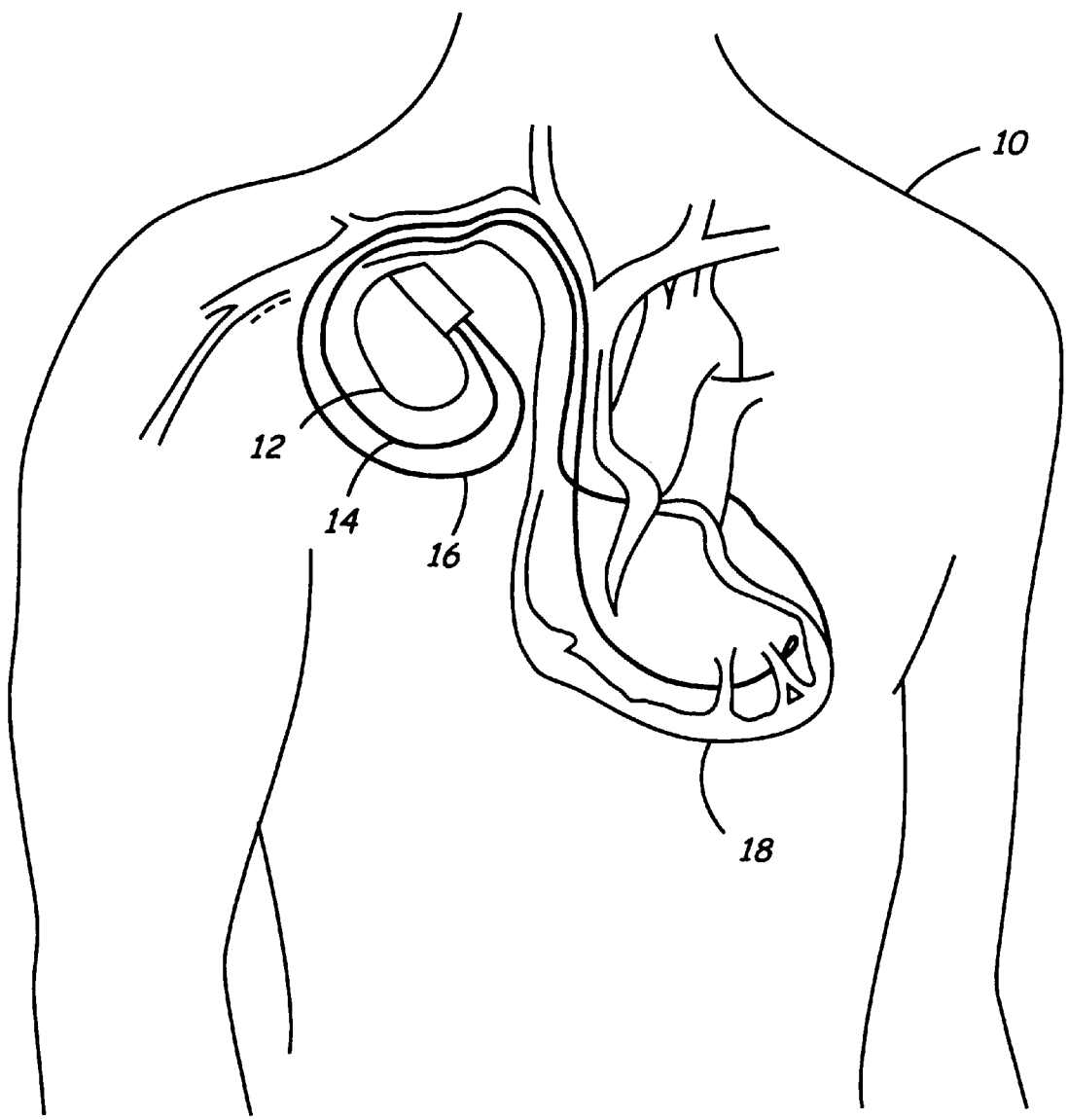
FIG. 1 is a schematic illustration of a typical implantation of an IPG and endocardial lead system in which the lead conductor construction and method of fracture detection of present invention is implemented.

FIG. 1 depicts a typical arrangement of a pacing or implantable cardioverter/defibrillator (ICD) system implanted in a patient 10, the system comprising a subcutaneously disposed implantable pulse generator (IPG) 12 and one or more endocardial atrial lead 14 and ventricular lead 16. The IPG 12 is implanted in a subcutaneous location in the upper chest as shown in FIG. 1 or in the abdomen, and the proximal ends of the endocardial leads 14 and 16 are coupled with it. The distal end of atrial lead 14 bearing one or more atrial pace/sense electrode is shown disposed generally in the atrial region of the patient's heart 18. The distal end of ventricular lead 16 bearing one or more pace/sense electrode is disposed generally in the ventricular region of heart 18. The distal end of lead 14 can also be disposed in the coronary sinus and even extend into a branching vein of the coronary sinus to dispose one or more distal pace/sense electrode in relation to the atrium or the ventricle to function as an atrial or ventricular pace/sense lead in a manner well known in the art. Alternatively, one or more of the leads 14 and 16 can disposed epicardially about the heart 18. Moreover, one or more of the endocardial leads 14 and 16 can include a cardioversion/defibrillation electrode disposed at any of the above described locations.

An exemplary cardioversion/defibrillation lead 20 in which the present invention may be advantageously implemented and that can be used in the locations of endocardial leads 14 and 16 is depicted in FIG. 2. Lead 20 is provided with an elongated insulating lead body 40, preferably fabricated of a plurality of co-extruded bio-compatible elastomers, as described further below, and enclosing at least three lead conductors. Although not visible in FIG. 2, it should be noted that the elongated conductors passing through lead body 40 may be any of the various known available conductors for use in conjunction with implantable electrical leads, including mono-filar or multi-filar coiled wire conductors, stranded wires formed of filaments, and the like as further described below with reference to FIG. 3.

An elongated cardioversion/defibrillation electrode 42, a pace/sense ring electrode 44, and a pace/sense tip electrode 46 are supported along a distal segment of the lead body 40 and are each coupled to a lead conductor located within the lead body 40. Electrodes 42, 44 and 46 may correspond to any conventionally available pace/sense and cardioversion/ defibrillation electrodes. When the lead 20 is intended for implantation in the right ventricular chamber, a fixation mechanism, e.g. the depicted soft, pliant tines 48 are provided to be lodged within right ventricular trabeculae to maintain electrode 46 in contact with the endocardium of the right ventricle. Alternatively, an active fixation mechanism, e.g., a retractable and rotatable helix, can be substituted for the tines 48, and the distal tip electrode can be fixed in the right atrial or ventricular heart chamber. The distal electrodes of the lead 40 can also be advanced into a cardiac vessel, e.g., the coronary sinus, if no fixation mechanism is provided.

A connector assembly is formed at the proximal end of the lead body 40 for making electrical and mechanical connection with the IPG 12 of FIG. 1 in a manner well known in the art. The connector assembly comprises a molded lead bifurcation which splits off two of the conductors within lead body 40 coupled to the distal pace/sense electrodes 44 and 46 to a bipolar, in-line connector assembly 24 which generally corresponds to the IS1 connector standard for pacing leads. Connector assembly 24 is provided with a first set of sealing rings 28, a connector ring 32, a second set of sealing rings 34, and connector pin 36. Connector pin 36 is coupled to the lead conductor that extends through the lead body 40 to the distal tip electrode 46. The connector ring 32 is coupled to the lead conductor that extends through the lead body 40 to pace/sense ring electrode 44. The lead conductor coupled to cardioversion/defibrillation electrode 42 extends to connector assembly 22 which comprises a set of sealing rings 26 and a connector pin 36. The illustrated connector assemblies 22 and 24 are conventional elements and may correspond to any of the numerous known electrical connector assemblies provided on implantable medical leads.

In the specific context of the lead 20 illustrated in FIG. 2, the lead conductor coupling connector pin 32 to distal electrode 16 preferably takes the form of a multi-filar, wire coil to allow passage of a stylet through a lumen of the wire coil. The lead conductors coupling ring electrode 14 to connector ring 32 and coupling the cardioversion/ defibrillation electrode 12 to connector pin 30 preferably take the same form or the form of stranded cables formed of wire filaments. But, the present invention is believed workable in the context of any of the numerous conductors known for use in implantable electrical leads, in any combination with one another, with or without the capability of receiving a stiffening stylet.

In conjunction with embodiments of the present invention which employ bundled, stranded conductors, interconnection of the conductors to the electrodes and connector rings may be accomplished by crimping, swaging and/or welding, as known to the art. In particular, interconnection of bundled, stranded conductors to connectors and electrodes may be accomplished according to U.S. patent application Ser. No. 08/439,332, filed May 11, 1995, by Swoyer et al., and in the above-incorporated '014 patent and in U.S. Pat. No. 5,676,694, all incorporated herein by reference.

The lead body 40 of the present invention is realized in a number of embodiments depicted in the cross-section views of FIGS. 3–8. In each case, the lead body 40 is formed as a lead body sheath that is co-extruded in a co-extrusion process using bio-compatible, electrically insulating, materials of differing durometers in differing axial sections thereof, resulting in a unitary lead body sheath having differing stiffness sections or areas or structures in its cross-section. The lead body sheath is co-extruded to provide a lead body outer surface 50 that is either exposed to the environment or enclosed within an outer sheath and to have a plurality of lead conductor lumens for receiving and enclosing a like plurality of lead conductors.

In FIG. 3, the lead body sheath 118 is co-extruded of three, for example, sheath segments 106, 108 and 110, each segment containing a lead conductor lumen and formed of a first durometer material. Sheath 118 is co-extruded with a web 120 of a second durometer material extending between the adjoining boundaries of the sheath segments 106, 108 and 110 and bonding the adjacent segments together into the unitary lead body insulating sheath 118. The web 120 may be formed by co-extrusion of the second durometer material, typically a higher durometer material than the first durometer material used to extrude the sheath segments 106, 108 and 110. The web 120 comprises three web arms 122, 124 and 126 that adhere to the adjoining sheath segment boundaries, while separating the adjoining sheath segment boundaries from one another.

The lead conductors 112, 114 and 116 illustrated in lead conductor lumens 100, 102 and 104 in the cross-section view of FIG. 3 are exemplary of lead conductor types that can be employed in the practice of the invention. All of the lead conductors 112, 114 and 116 are formed in an electrically redundant manner of a plurality of wire coiled wires or stranded wire filaments that are coated on their exterior surfaces with PTFE to facilitate inserting the lead conductors through the lead conductor lumens 100, 102 and 104, respectively.

Two different versions of straight lead conductors 112 and 114 are depicted in the lead conductor lumens 100 and 102, respectively. Each of the straight conductors 112 and 114 may take the form of a bundled, stranded filament conductors disclosed in the above-incorporated '986 and '321 patents or the '829 application, for example. The invention may also be practiced using any of the numerous other stranded filament conductors known to the art. The stranded filament conductors of the present invention can also be wound into a plurality of intertwined, parallel wound, coils that are electrically connected together as described above with respect to the above-incorporated '983 and '022 patents, for example. The lead conductor 114 is formed of a straight, inner core filament 142 surrounded by six outer filaments 144, 146, 148, 150,152 and 154 helically wound into a single 1×7 wire strand or cable. The lead conductor 112 is formed in the manner described in the above-incorporated '414 patent of seven strands, and each strand is formed of seven filaments of smaller gauge than those forming lead conductor 114, resulting in a "7×7" wire cable of 49 total filaments. The straight, centrally disposed, core wire strand 128 is formed of six outer filaments helically wound around a straight inner core filament. The six outer or perimeter wire strands 130, 132, 134, 136, 138, and 140 are formed in the same manner as the core wire strand 128, that is, by an inner core filament surrounded by six outer filaments that are helically wound about it. The six outer or perimeter wire strands 130, 132, 134, 136, 138, and 140 are themselves wound helically around the straight core wire strand 128.

Lead conductor 116 is formed in a parallel wound, multi-filar, coiled wire of the type disclosed in the above-incorporated '435 patent. The four parallel wound wires 156, 158, 160 and 162 are electrically connected together at the proximal connection with one of the proximal connector elements and distal connection with one of the distal electrodes.

Each of the conductive wires or filaments can be formed of a single alloy material or formed as depicted with an inner core of a highly conductive alloy or metal, e.g. silver, surrounded by an outer sheath of another conductor, e.g., stainless steel or MP35N alloy, that is more resistant to degradation using the DBS or the drawn-filled-tube (DFT) extrusion techniques described in the above-incorporated '044 patent as is well known in the art. The current carrying capacity of cardioversion/defibrillation lead conductors, e.g. the stranded filament and cable conductors 114 and 112 formed in these ways is maximized for the cross-section dimensions of the individual filaments and cables.

These differing lead conductors 112, 114 and 116 are merely exemplary of different lead conductor types that may be employed in any combination in the lead conductor lumens 100, 102 and 104 and any further lead conductor lumens that can be formed in the insulating lead body sheath 118. Such lead conductor types have differing outer diameters and bending stiffness characteristics.

The extrusion of the insulating lead body sheath 118 of the lead body 40 can be effected in many ways in accordance with the present invention. In the first embodiment depicted in FIG. 3, the insulating sheath 118 the lead body sheath is co-extruded of the plurality of arcuate or pie piece shaped, sheath segments 106, 108 and 110 in which the lead conductor lumens 100, 102 and 104 are formed. Each segment 106, 108 and 110 is formed of the same elastomeric material, e.g. a polyurethane a first durometer. The arms 122, 124 and 126 of web 120 are co-extruded of a second durometer material between the adjoining boundaries of the sheath segments 106, 108 and 110 to bond them together into the unitary lead body insulating sheath 118. The Y-shaped web 120 is depicted schematically and can be of any suitable width that strengthens the lead body 40.

The web 120 is preferably formed by co-extrusion of a single second durometer material, typically a higher durometer material than the first durometer material of the sheath segments 106, 108 and 110. However, it will be understood that the arms 122, 124 and 126 can be co-extruded separately of differing materials that are tailored, in this instance in durometer to complement and offset bending characteristics of the lead conductors 112, 114 and 116 or to otherwise affect the bending characteristics of the lead body 40.

Also, in the depicted view of this embodiment, the ends of the arms 122, 124 and 126 of web 120 extend to and becomes part of the exposed lead body surface 50. However, it will be understood that the outer ends of the arms 122, 124 and 126 can terminate within the sheath body 118 such that the adjoining sheath segments 106, 108 and 110 merge together in a peripheral band adjacent to the exposed lead body surface 50 and totally enclose the web 120.

Figure 4:
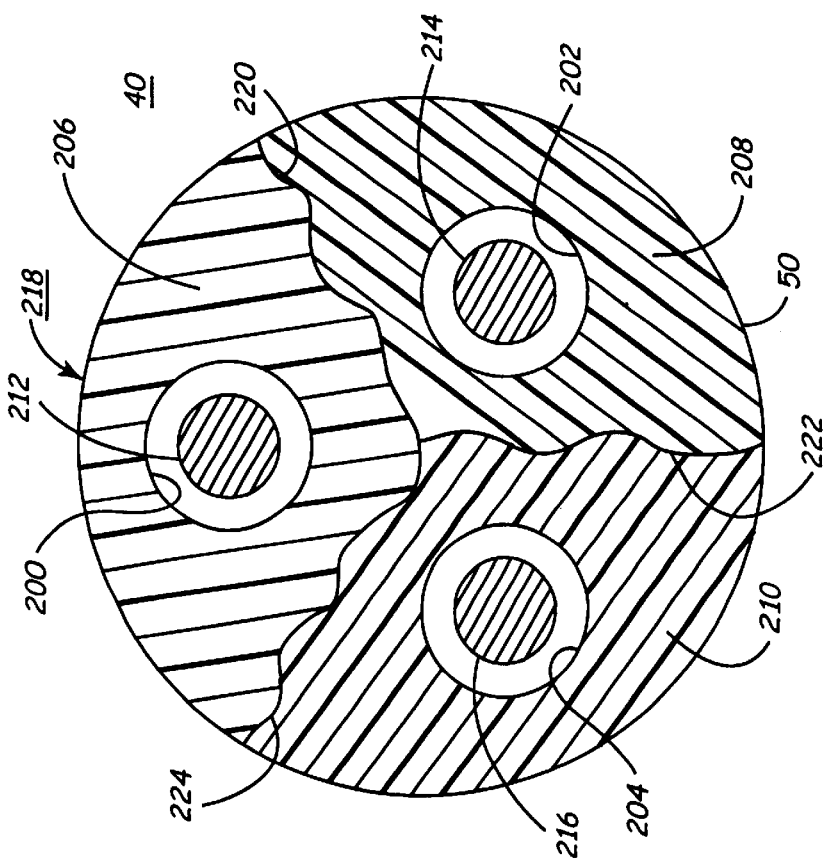

In a first variation of the further embodiment depicted in FIG. 4, the lead body sheath 218 is co-extruded of a plurality of sheath segments 206, 208 and 210 enclosing lead conductor lumens 200, 202 and 204, respectively. Each sheath segment 206 is formed of a selected durometer material, whereby the lead body sheath 218 as a whole can be tailored to exhibit differing bending flexibilities away from the lead body sheath axis (perpendicular to the plane of the cross-section view) in selected polar directions around the 360° circumference of the sheath body 218. As a result of the co-extrusion process, the sheath segments 206, 208 and 210 are bounded by and form the exposed surface 50 and the boundaries 220, 222 and 224.

The lead conductors 212, 214 and 216 are shown schematically in this view and may take any of the known forms described herein or otherwise known in the art at the time of filing this application for patent and that become known thereafter. This embodiment and the following described variations are particularly suitable for use with above described lead conductors of differing types that have differing bending stiffnesses. In one application of this embodiment, the durometers of the sheath segments 206, 208 and 210 are selected in relation to the lead conductor to compensate for the lead conductor bending stiffness. For example, relatively stiff lead conductors can be enclosed in segment lumens formed within segments of relatively low stiffness due to relatively low durometer materials, whereas relatively flexible lead conductors can be enclosed in segment lumens formed within segments of relatively high stiffness due to relatively high durometer materials. In this way, the bending stiffness of the lead body 40 in all polar directions through 360° can be brought into equilibrium.

In a further application of this embodiment, it may be desired to form a lead body that does exhibit a bias to bend more readily in one polar direction than in the other directions. In this case, one of the sheath segments 206, 208 and 210 can be co-extruded of a more flexible material than the other sheath segments, and can enclose a relatively flexible lead conductor within that sheath segment lumen.

Figure 5:
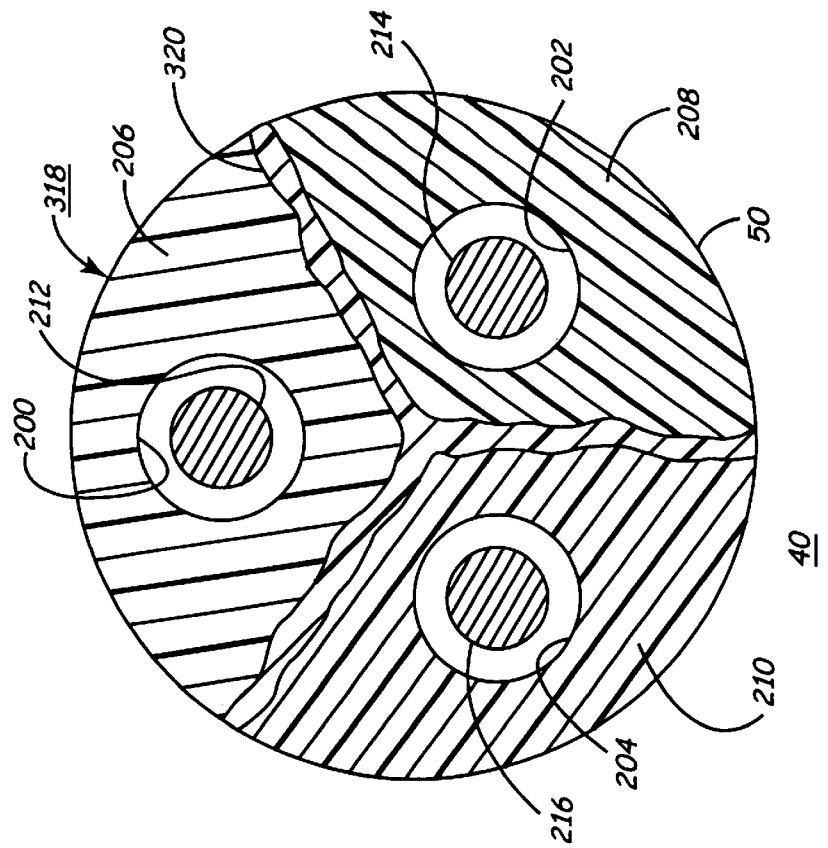

In the third embodiment of an insulating sheath 318 is depicted in FIG. 5, wherein a web 320 like web 120 of the first embodiment is employed to strengthen the boundary between the adjacent lead conductor lumens 200, 202 and 204 while providing the differing stiffness sheath segment materials of the second embodiment. The web 320 can be formed of any suitable durometer material that is compatible with and can be co-extruded with the materials of the sheath segments 206, 208 and 210.

Figure 6:
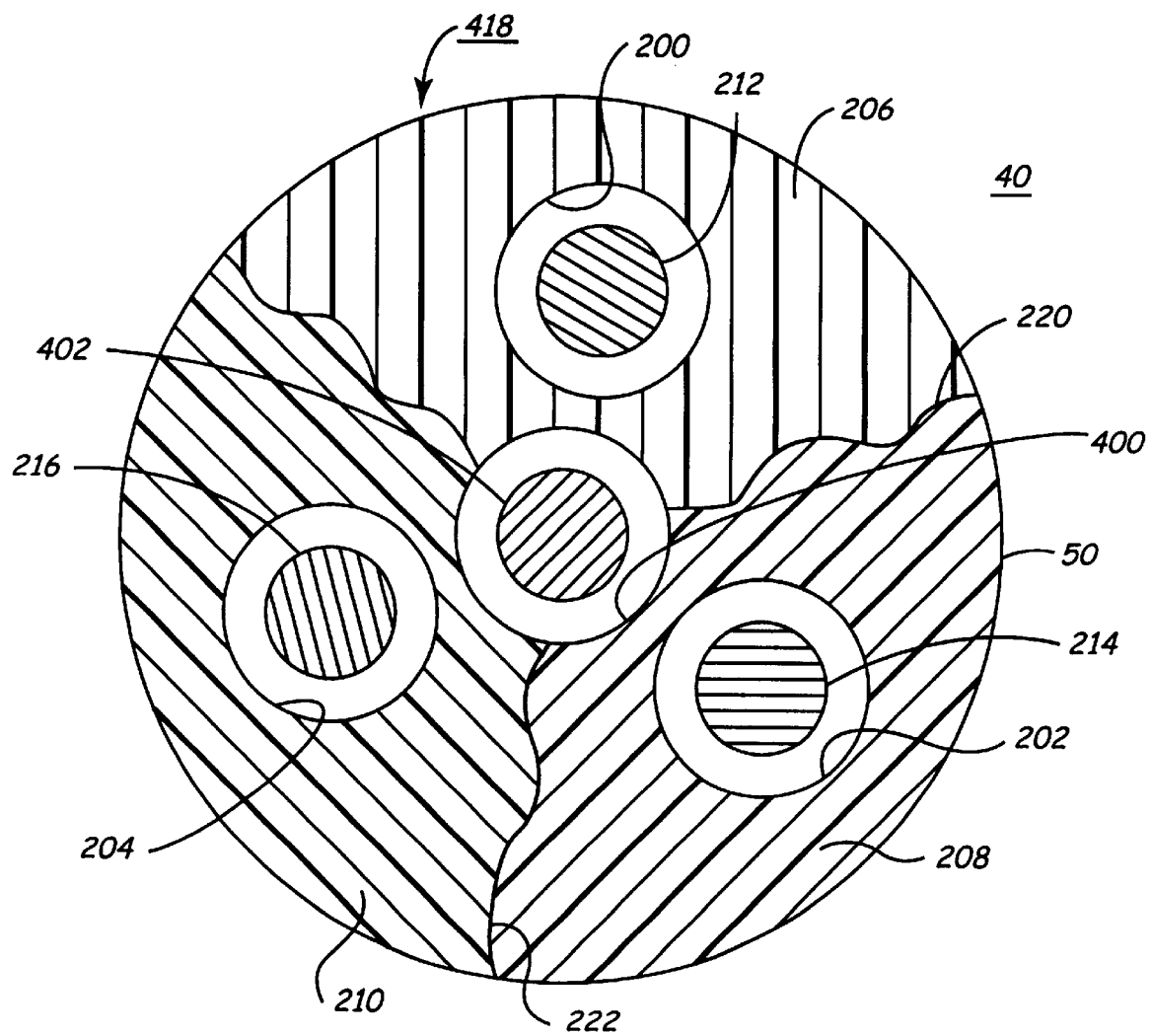
Figure 7:
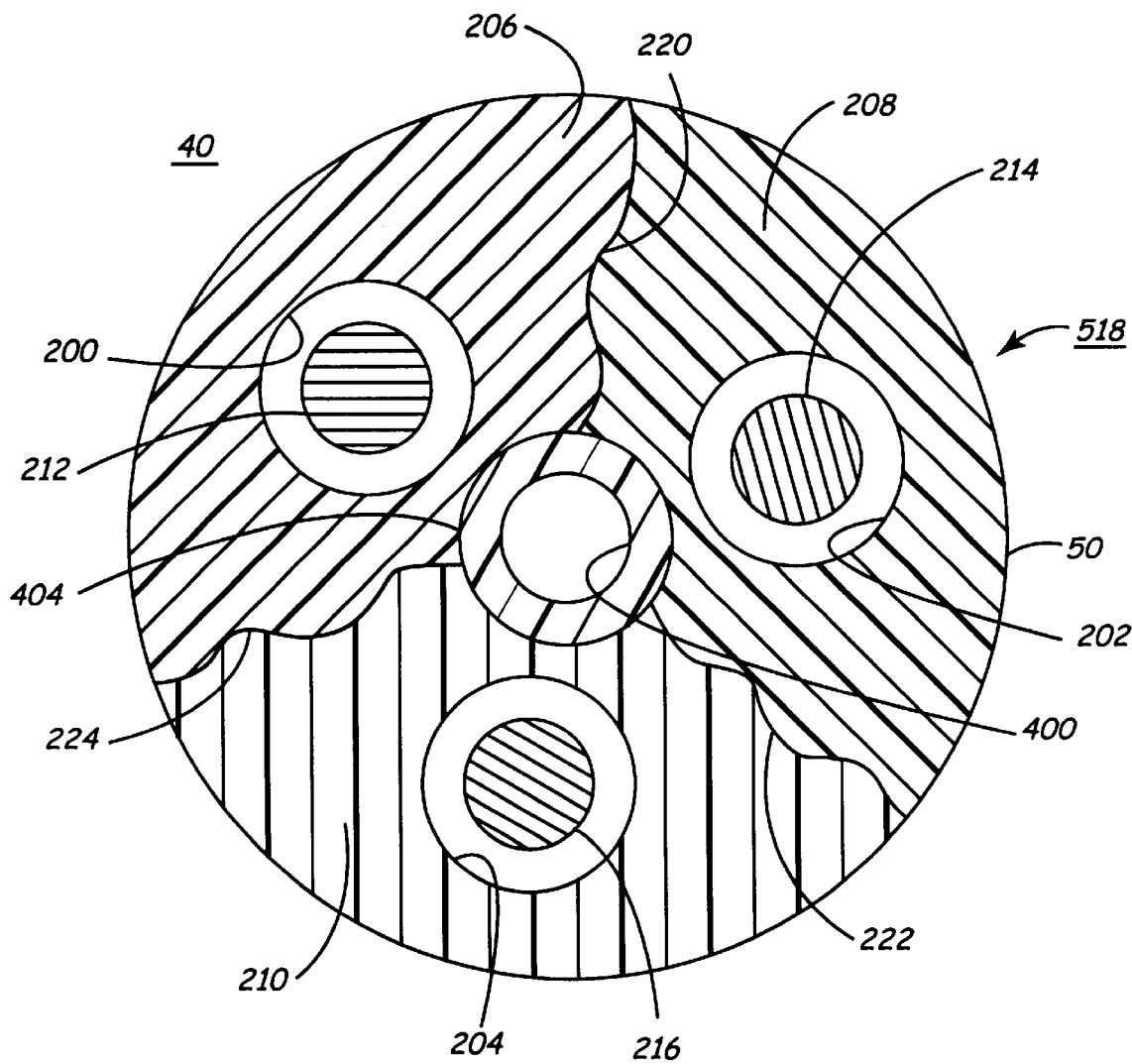
Figure 8:
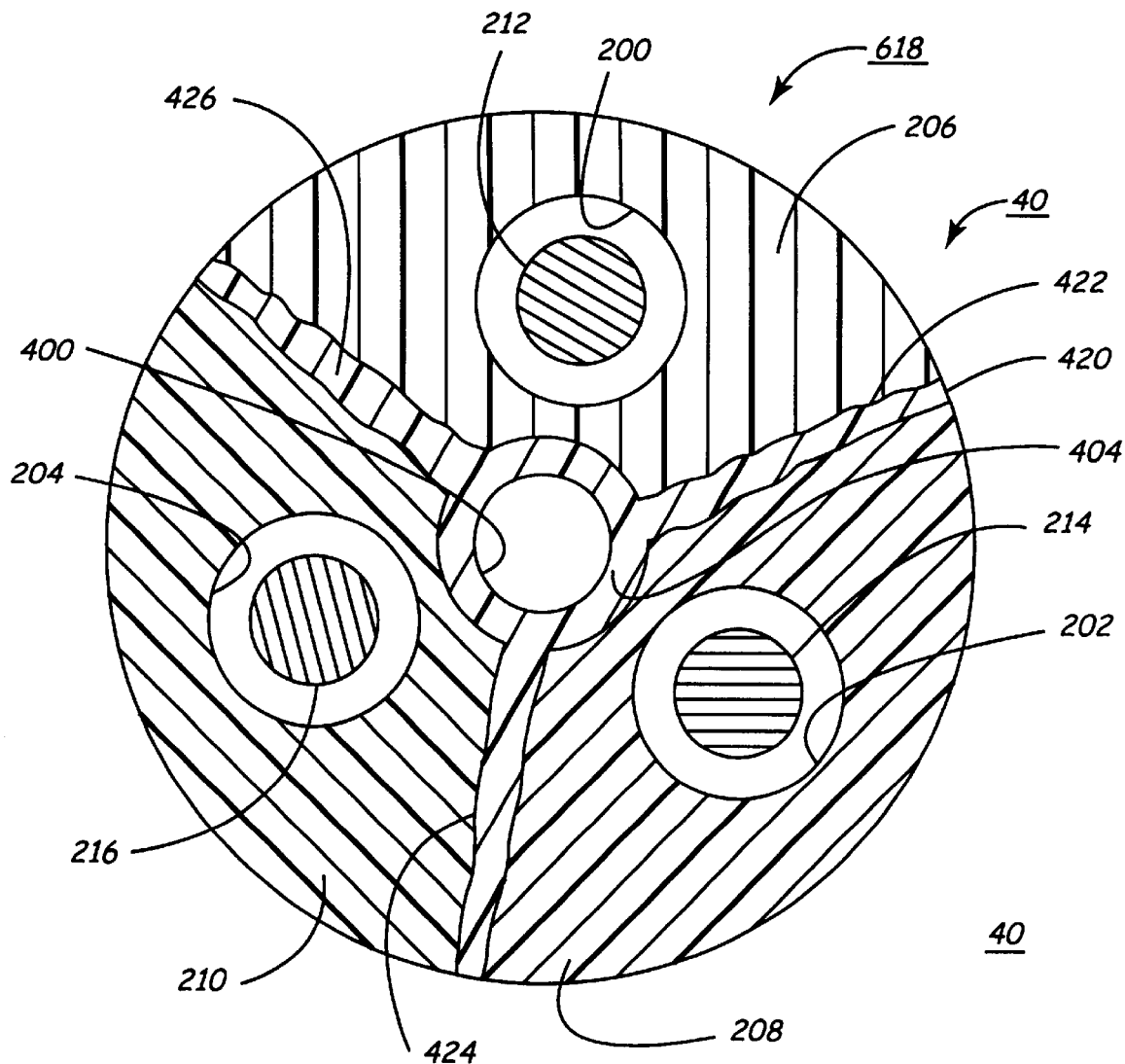

In the three variations of a fourth embodiment depicted in FIGS. 6–8, a centrally located lead conductor and/or stiffening stylet receiving lumen 400 can also be formed of the same or differing durometer material as the sheath segments of the first or second embodiment or surrounded by the web material of the first or third embodiment. In FIG. 6, the insulating sheath 418 is formed in the manner of the embodiment of FIG. 4 except that the centrally disposed lumen 400 is formed therein. In FIG. 7, the insulating sheath 518 is formed in the same manner as the embodiment of FIG. 6, except that the central lumen 400 is surrounded by a tube 404 of differing durometer than those of the three sheath segments 206, 208 and 210.

In the further variation of the insulating sheath 618 depicted in FIG. 8, a Y-shaped web 420 is formed of three arms 422, 424 and 426 extending from the tube 404 surrounding the central lumen 400. The arms 422, 424 and 426 are preferably extruded of the material of the tube 404. However, they could be formed separately of materials tailored to complement the materials forming the sheath segments 206, 208 and 210.

In a further variation of FIG. 8, the sheath segments 206, 208 and 210 could be formed of the same material as taught in the first embodiment of FIG. 3. Moreover, the outer ends of the three arms 422, 424 and 426 extending from the tube 404 surrounding the central lumen 400 could be shortened so that the material used to extrude the segments 206, 208 and 210 merge together in a band adjacent to the outer surface 50.

In these embodiments of FIGS. 6–8, central lumen 400 would extend through lead body 40 to the lumen of proximal connector pin 36 and would be adapted to receive a stiffening stylet or lead conductor or both as represented by element 402. For example, the coiled wire lead conductor 116 of FIG. 3 would advantageously be disposed in central lumen 400 to use that lumen as a conductor lumen while still providing a lumen for receiving a stiffening stylet in a manner well known in the art.

In the embodiments and variations depicted in FIGS. 4–8, the sheath segments 206, 208 and 210 are depicted as being formed of different durometer elastomeric materials that are co-extruded together with or without a web 220 and/or tube 404 surrounding the central lumen 400. It will be understood that two of the illustrated three segments 206, 208 and 210 could be formed of the same durometer hardness material It will also be understood that only two or more than three such sheath segments can be formed in the lead body sheath in accordance with the teachings of the present invention.

The elastomeric insulating sheaths 118, 218, 318, 418, 518, 618 and the above-described variations thereof can be fabricated using co-extrusion techniques that are well known in the art. For example, U.S. Pat. Nos. 4,790,831, 5,546,674 and 5,622,665 disclose exemplary extrusion and co-extrusion techniques that are employed in the co-extrusion of side walls of catheter bodies for selectively altering the side wall characteristics around its circumference.

Acceptable polyurethane elastomers comprise polyether urethane elastomers having a durometer on the Shore A durometer scale of at least about 80A or a substantially ether-free polyurethane elastomer. The elastomer must also be hydrolically stable, not oxidize, and have a toughness in the range of polyurethanes generally. A suitable urethane is Pellethane 2363-55D or Pellethane 2363-55DE of Dow Chemical Co. of Midland, Mich. Polyurethanes essentially equivalent to Pellethane 2363-55D are available from other sources such as B. F. Goodrich, Inc. The Pellethane 2363 family of polymers, including 2363-80A and 2363-55D, are composed of methylene bis-isocyanato benzene (MDI), butane diol (BD) hard segments and polytetramethylene ether oxide (PTMO) soft segments. The proportion of hard to soft segments is higher for the harder (Shore 55D) polymer than for the softer (Shore 80A) material thereby providing fewer ether linkages which may be subject to in vivo degradation.

Preferably, the urethane is a substantially ether-free polyurethane since stress cracking appears to have a relation to the ether content of the polymer, with fewer ether linkages being desirable. A polymer without ether linkages may be made by substituting aliphatic, polycarbonate or polydimethylsiloxane groups for the polyether groups of the soft segments. Ether-free polyurethanes said to be suitable for in vivo use are disclosed in U.S. Pat. Nos. 4,873,308, 5,109, 077, and 5,133,742, and in published International Patent Application WO 92/04390, all incorporated herein by reference in their entirety. Biostable ether-free polymers include PolyMedica's Chronoflex AL-80A and Chronoflex AL-55D, the family of biostable polyurethanes disclosed in the above-incorporated '308 patent and AKZO/ENKA'S PUR series of polyurethanes. These materials can be coated over the preferred lead insulator material, Pellethane 2363-80A, by methods such as solution coating or co-extrusion.

In accordance with the method of the present invention, the lead body sheath 118, 218, 318, 418, 518, 618 is fabricated to form each of the sheath cross-sections depicted in FIGS. 3–8 and above-described variations thereof using such co-extrusion techniques. The selected lead conductors are inserted through the sheath lumens for the length of the lead body sheath to form the lead body 40. Surface electrodes, e.g. the distal ring electrode 44 and the elongated cardioversion/defibrillation electrode 42 are formed over the distal exterior surface 50 and electrically attached to the distal ends of the appropriate lead conductors. The distal tip electrode 46 is electrically attached to the distal end of the appropriate lead conductor, and the distal electrode 46 and fixation mechanism, e.g. the tines 48, are mechanically attached to the distal end of the lead body 40. The proximal end of the lead body 40 is attached to the proximal connector assemblies 22 and 24 in a manner well known in the art.

The principles of the present invention can also be applied to the fabrication of an insulating sheath comprising an inner core surrounded by an external sheath as disclosed in the above-incorporated U.S. patent application Ser. No. 08/990,647. The inner core can be fabricated in the co-extrusion process to have a plurality of sheath segments as described above in reference to FIGS. 3–8 but having a lead conductor receiving groove, rather than a fully enclosed lead conductor lumen formed therein. The inner core and lead conductors fitted into the grooves are encased within an outer tubing member of an elastomeric material.

Although particular embodiments of the invention have been described herein in some detail, this has been done for the purpose of providing a written description of the invention in an enabling manner and to form a basis for establishing equivalents to structure and method steps not specifically described or listed. It is contemplated by the inventors that the scope of the limitations of the following claims encompasses the described embodiments and equivalents thereto now known and coming into existence during the term of the patent. Thus, it is expected that various changes, alterations, or modifications may be made to the invention as described herein without departing from the spirit and scope of the invention as defined by the appended claims.

What is claimed is:

1. In a medical electrical lead for implantation within the living body of the type comprising an elongated lead body enclosing a plurality of lead conductors each extending between a distal a distal electrode or sensor element and a proximal connector element, the improvement in the lead body comprising:

an elongated lead body sheath having an outer sheath surface that is formed of a plurality of axial sheath segments each co-extruded of a bio-compatible, electrically insulating, material, the plurality of axial sheath segments extending in side by side relation through the length of the lead body and bonded together at adjoining segment boundaries;

a like plurality of elongated lead conductor lumens formed in and extending the length of each lead body sheath segment to be enclosed thereby; and a like plurality of electrical lead conductors, each lead conductor extending through a lead conductor lumen.

2. The medical electrical lead of claim 1, wherein at least two of the axial sheath segments are formed of materials of differing durometers.

3. The medical electrical lead of claim 2, wherein at least two of the lead conductors have differing bending stiffnesses.

4. The medical electrical lead of claim 1, wherein said plurality of lead conductors comprises a first lead conductor having a first bending stiffness that differs from the stiffnesses of the remaining lead conductors of the plurality of lead conductors; and said plurality of axial sheath segments comprises a first axial sheath segment having a first lead lumen receiving the first lead conductor, the first axial segment formed of a material having a hardness that is correlated to the first bending stiffness.

5. The medical electrical lead of claim 1, wherein each one of said plurality of lead conductors have a bending stiffness that differs from the bending stiffnesses of the remaining lead conductors of the plurality of lead conductors; and each one of said plurality of axial sheath segments are formed of a material having a hardness that is correlated to the bending stiffness of the lead conductor received in the lead conductor lumen of the axial sheath segment.

6. The medical electrical lead of claim 1, further comprising a further lumen formed centrally in said lead body sheath.

7. The medical electrical lead of claim 6, wherein at least two of the axial sheath segments are formed of materials of differing durometers.

8. The medical electrical lead of claim 7, wherein at least two of the lead conductors have differing bending stiffnesses.

9. The medical electrical lead of claim 6, wherein said plurality of lead conductors comprises a first lead conductor having a first bending stiffness that differs from the stiffnesses of the remaining lead conductors of the plurality of lead conductors; and said plurality of axial sheath segments comprises a first axial sheath segment having a first lead lumen receiving the first lead conductor, the first axial segment formed of a material having a hardness that is correlated to the first bending stiffness.

10. The medical electrical lead of claim 6, wherein each one of said plurality of lead conductors have a bending stiffness that differs from the bending stiffnesses of the remaining lead conductors of the plurality of lead conductors; and each one of said plurality of axial sheath segments are formed of a material having a hardness that is correlated to the bending stiffness of the lead conductor received in the lead conductor lumen of the axial sheath segment.

11. The medical electrical lead of claim 1, further comprising a tubular member enclosing a further lumen formed centrally in said lead body sheath.

12. The medical electrical lead of claim 11, wherein at least two of the axial sheath segments are formed of materials of differing durometers.

13. The medical electrical lead of claim 12, wherein at least two of the lead conductors have differing bending stiffnesses.

14. The medical electrical lead of claim 11, wherein said plurality of lead conductors comprises a first lead conductor having a first bending stiffness that differs from the stiffnesses of the remaining lead conductors of the plurality of lead conductors; and said plurality of axial sheath segments comprises a first axial sheath segment having a first lead lumen receiving the first lead conductor, the first axial segment formed of a material having a hardness that is correlated to the first bending stiffness.

15. The medical electrical lead of claim 11, wherein each one of said plurality of lead conductors have a bending stiffness that differs from the bending stiffnesses of the remaining lead conductors of the plurality of lead conductors; and each one of said plurality of axial sheath segments are formed of a material having a hardness that is correlated to the bending stiffness of the lead conductor received in the lead conductor lumen of the axial sheath segment.

16. A method of manufacturing the lead body of a medical electrical lead for implantation within the living body of the type comprising an elongated lead body enclosing a plurality of lead conductors each extending between a distal a distal electrode or sensor element and a proximal connector element, the method comprising the steps of:

co-extruding a plurality of axial sheath segments of a bio-compatible, electrically insulating, material each with a lead conductor lumen into an elongated lead body sheath that is formed of the plurality of axial sheath segments extending in side by side relation through the length of the lead body and bonded together at adjoining boundaries and enclosing a like plurality of elongated lead conductor lumens; and fitting each one of a like plurality of electrical lead conductors through a lead conductor lumen.

17. The method of claim 16, wherein the co-extruding step further comprises the step of co-extruding at least two of the axial sheath segments of materials of differing hardness.

18. The method of claim 17, wherein at least two of the lead conductors have differing bending stiffnesses.

19. The method of claim 16, wherein said plurality of lead conductors comprises a first lead conductor having a first bending stiffness that differs from the stiffnesses of the remaining lead conductors of the plurality of lead conductors; and wherein the co-extruding step further comprises the step of co-extruding said plurality of axial sheath segments with a first axial sheath segment having a first lead lumen receiving the first lead conductor, the first axial segment formed of a material having a hardness that is correlated to the first bending stiffness.

20. The method of claim 16, wherein each one of said plurality of lead conductors have a bending stiffness that differs from the bending stiffnesses of the remaining lead conductors of the plurality of lead conductors; and wherein the co-extruding step further comprises the step of co-extruding each one of said plurality of axial sheath segments of a material having a hardness that is correlated to the bending stiffness of the lead conductor received in the lead conductor lumen of the axial sheath segment.

21. The method of claim 16, wherein the co-extruding step further comprises the step of co-extruding a further lumen centrally in said lead body sheath.

* * * * *